US012580073B2

(12) United States Patent　　(10) Patent No.:　US 12,580,073 B2
Schneider　　(45) Date of Patent:　Mar. 17, 2026

(54) METHOD OF IDENTIFYING DENTAL CONSUMABLES EQUIPPED INTO A DENTAL TOOL MACHINE

(71) Applicants: DENTSPLY SIRONA INC., York, PA (US); SIRONA DENTAL SYSTEMS GMBH, Bensheim (DE)

(72) Inventor: Hans-Christian Schneider, Einhausen (DE)

(73) Assignee: Dentsply Sirona Inc., York, PA (US)

( * ) Notice: Subject to any disclaimer, the term of this patent is extended or adjusted under 35 U.S.C. 154(b) by 494 days.

(21) Appl. No.: 17/765,527

(22) PCT Filed: Oct. 14, 2020

(86) PCT No.: PCT/EP2020/078890
§ 371 (c)(1),
(2) Date: Mar. 31, 2022

(87) PCT Pub. No.: WO2021/078604
PCT Pub. Date: Apr. 29, 2021

(65) Prior Publication Data
US 2022/0359065 A1　Nov. 10, 2022

(30) Foreign Application Priority Data
Oct. 23, 2019　(EP) ..................................... 19204901

(51) Int. Cl.
*G16H 40/20*　(2018.01)
*G06K 7/10*　(2006.01)
*G06K 7/14*　(2006.01)
(52) U.S. Cl.
CPC ......... *G16H 40/20* (2018.01); *G06K 7/10366* (2013.01); *G06K 7/1413* (2013.01); *G06K 7/1417* (2013.01)

(58) Field of Classification Search
CPC .. G16H 40/20; G06K 7/10366; G06K 7/1413; G06K 7/1417; G06K 19/06;
(Continued)

(56) References Cited

U.S. PATENT DOCUMENTS

2003/0060920 A1*　3/2003　Kishlyansky .......... G01H 1/003
702/56
2010/0297580 A1　11/2010　Niewiadomski
(Continued)

FOREIGN PATENT DOCUMENTS

CA　　3153617　　4/2021
CN　　104736098 A　6/2015
(Continued)

OTHER PUBLICATIONS

International Search Report; PCT/EP2020/078890; Nov. 18, 2020 (completed); Nov. 30, 2020 (mailed).
(Continued)

*Primary Examiner* — Thomas C Lee
*Assistant Examiner* — Tyler Dean Hedrick
(74) *Attorney, Agent, or Firm* — SCHWEGMAN LUNDBERG & WOESSNER, P.A.

(57) ABSTRACT

A method of identifying dental consumables including at least one of a dental blank (2) and a dental tool (3) equipped into a dental tool machine (1). The method includes: a step of colliding the dental tool (3) with the dental blank (2) or a dental blank holder of the dental tool machine (1) and a step of detecting a signal indicative of the collision. The method also includes a step of analyzing the detected signal through trained artificial intelligence; and a step of identifying the type and/or condition of at least one of the dental consumables based on the analysis.

20 Claims, 2 Drawing Sheets

(58) Field of Classification Search
CPC ........... A61C 13/0004; A61C 13/0022; G05B
2219/35021; G05B 2219/45167; G05B
2219/49296; G05B 2219/49302; G05B
19/401; G06N 3/045; G06N 3/08
See application file for complete search history.

(56) References Cited

U.S. PATENT DOCUMENTS

| | | | |
|---|---|---|---|
| 2011/0250398 A1 | 10/2011 | Basler | |
| 2016/0067017 A1 | 3/2016 | Niewiadomski | |
| 2017/0320182 A1* | 11/2017 | Jeong ................... | B23Q 17/098 |
| 2018/0092710 A1 | 4/2018 | Bosisio et al. | |
| 2018/0168401 A1* | 6/2018 | Weiss ................... | A47J 43/288 |
| 2019/0366554 A1* | 12/2019 | Breugelmans ......... | B25J 9/1679 |
| 2020/0206833 A1* | 7/2020 | Dey, IV ................ | B23D 51/16 |
| 2022/0009049 A1* | 1/2022 | Liu .................... | G05B 19/4065 |
| 2022/0043425 A1* | 2/2022 | Trecapelli ............. | B23Q 15/08 |

FOREIGN PATENT DOCUMENTS

| | | | | |
|---|---|---|---|---|
| CN | 114585325 | | 4/2025 | |
| DE | 102016124274 A1 * | 6/2018 | .............. | G01N 3/30 |
| EP | 3812859 A1 | | 4/2021 | |
| EP | 3812859 B1 | | 11/2023 | |
| JP | S60183591 | | 9/1985 | |
| JP | 2006175238 | | 7/2006 | |
| WO | 2014006579 A2 | | 1/2014 | |
| WO | WO-2021078604 A1 | | 4/2021 | |

OTHER PUBLICATIONS

Written Opinion of the International Searching Authority; PCT/EP2020/078890; Nov. 18, 2020 (completed); Nov. 30, 2020 (mailed).
International Preliminary Report on Patentability; PCT/EP2020/078890; Nov. 18, 2020 (completed); Nov. 30, 2020 (mailed.
Chinese Office Action dated Jan. 30, 2024.
"European Application Serial No. 19204901.3, Extended European Search Report mailed Apr. 7, 2020", 8 pgs.
"Chinese Application Serial No. 202080074023.0, Response filed Feb. 7, 2025 to Office Action mailed Dec. 10, 2024", W/ English Claims, 16 pgs.
"Japanese Application Serial No. 2022-522969, Response filed Mar. 17, 2025 to Notification of Reasons for Rejection mailed Dec. 17, 2024", W/English Claims, 10 pgs.
"Chinese Application Serial No. 202080074023.0, Office Action mailed Dec. 10, 2024", w English Translation, 21 pgs.
"Japanese Application Serial No. 2022-522969, Notification of Reasons for Rejection mailed Dec. 17, 2024", W English Translation, 6 pgs.

* cited by examiner

METHOD OF IDENTIFYING DENTAL CONSUMABLES EQUIPPED INTO A DENTAL TOOL MACHINE

CROSS-REFERENCE TO RELATED APPLICATIONS

This is a National Phase application of International Application No. PCT/EP2020/078890, filed Oct. 14, 2020, which claims the benefit of and priority to European Application Ser. No. 19204901.3, filed on Oct. 23, 2019, which are herein incorporated by reference for all purposes.

TECHNICAL FIELD OF THE INVENTION

The present invention relates to a dental machining system which has a dental tool machine for manufacturing a dental restoration from a dental blank by using one or more dental tools. The present invention more particularly relates to a method of identifying dental consumables such as the dental tools and the dental blanks equipped into the dental tool machine.

BACKGROUND OF THE INVENTION

In general, a dental machining system has a dental tool machine for machining a dental blank which is typically made from ceramic. The dental tool machine generally has one or more driving units each movably holding at least one dental tool for machining a corresponding side of the dental blank. The dental tools are respectively mounted to tool motors in the driving units. The dental tools can be exchanged after their service lifes are over. The dental blank is mounted to a dental blank holder which is relatively movable with respect to the dental tools. A control means controls the operation of the dental tool machine. Generally, a CAD/CAM software is used to digitally construct a dental restoration and to provide the corresponding machining data to the dental tool machine. The CAD/CAM software is usually run on a processing unit such as a PC in the dental machining system.

The dental blank and the dental tool are consumables of the dental tool machine. The dental consumables which are available on the market vary in size, shape, and material. The dental tool machine must be equipped by the operator with the correct dental blank and the correct dental tool that match the specific requirements of the machining. When equipping the dental tool machine, the operator usually selects the correct dental consumables via the user interface from a database managed by the CAD/CAM software which partly serves as an auxiliary recognition means. Thereby, the information on the dental consumables equipped into the dental tool machine is also input to the dental tool machine, and thus recognized by the dental tool machine. However, there is a risk that the user inputs wrong information into the dental tool machine. Alternatively, each dental consumable is recognized by a reading means that reads the information tag of the dental consumable which also serves as an auxiliary recognition means. The information tag may be, for example, an RFID tag, a QR code, a bar code or the like. The reading means may be an RF transceiver or an optical transceiver, a camera or the like. The reading means may be located in the control panel such that the operator can approach the information tag of the dental consumable to the control panel for the reading operation before equipping it into the dental tool machine. However, there is a risk that the user mixes up the dental consumables after the reading operation and before equipping them into the dental tool machine. Alternatively, the reading means may be positioned close to the mounting positions of the dental consumables so that the information tags can be read after equipping them into the dental tool machine. However, the integration of the reading means into the machining compartment increases the costs. Furthermore, the reading means, and the information tags increase the overall cost of the dental machining system.

In general, the dental tool machine conducts a "touch-process" for calibration purposes prior to the start of the machining. In the touch-process, slowly rotating dental tools are moved against the dental blank on the defined axes of freedom. During the touch-process, the collision between dental blank and dental tool is detected through a sensor that generates a signal using a reference value. The signal is usually generated by using an acoustic sensor such as a microphone. At each collision, the position of the dental tool is recorded by the control means by using position encoders of the dental machine, and thus the dental blank is geometrically measured. The dental tool can also be measured by colliding it in a controlled manner with a precision mechanical part of the dental tool machine e.g. the dental blank holder on the machine side or the dental blank side. Through the touch-process, it is generally possible to recognize incorrect dental blank sizes or broken dental tools but not the wrong dental blank material or a blunt dental tool.

If the dental consumables don't match the specific requirements of the machining, then there is a risk that the dental restoration can't be machined with the desired quality. In the worst case, the dental tool may be overrun its total service life or its remaining service life if it has been previously used in a preceding machining process. In such events, the dental tool will break, and the dental restoration will receive damages. In less severe cases, the machining of the dental restoration is completed with an unacceptable, low quality due to the use of the inadequate dental consumables. In all these cases, the user satisfaction may decrease, and the users may complain about the quality.

SUMMARY OF THE INVENTION

An objective of the present invention is to overcome the problems of the prior art as much as possible and to provide a method of identifying dental consumables such as dental tools and dental blanks equipped into a dental tool machine.

This objective is achieved through the method as defined in claim 1, and the dental machining system as defined in claim 17. The subject-matters of the other claims relate to further developments.

The present invention provides a method of identifying dental consumables including at least one of a dental blank and a dental tool equipped into a dental tool machine. The method comprises a step of colliding the dental tool with the dental blank or a dental blank holder of the dental tool machine; a step of detecting a signal indicative of the collision; a step of analyzing the detected signal through trained artificial intelligence; and a step of identifying the type and/or the condition of at least one of the dental consumables based on the analysis.

A major advantageous effect of the present invention is that the touch-process can be used in combination with the trained artificial intelligence to identify the type and/or the condition of the consumable equipped into the dental tool machine. Thereby, the geometrical measurement of the dental blank and, optionally, the calibration of the dental tool machine can be carried out simultaneously with the identification of the dental consumables. Thereby, the machining of the dental blank can be started comparatively earlier, and the overall processing time can be reduced. Another major advantageous effect of the present invention is that the identification tags on the dental consumables such as the RFID tags, QR codes, bar codes, and the associated reading means such as the RF transceivers, the optical transceiver, the camera in the dental tool machine can be omitted. Thereby, the performance cost ratio can also be improved. Thereby, also the risk of using counterfeit consumables can be reduced. Another major advantageous effect of the present invention is that the need for manually inputting information on the dental consumables into the dental tool machine can also be omitted. Thereby, the identification of the consumables can be achieved in a user interaction free manner and more quickly. Thereby, the dental tool machine becomes more user friendly. Thereby, the risk of inputting any incorrect information can also be prevented, and the machining can be conducted more safely. Another major advantageous effect of the present invention is that the risk of using blunt dental tools can be prevented, and thus the risk of damaging the dental restoration and/or the dental tool can be avoided or reduced as much as possible. Another major advantageous effect of the present invention is that the unqualified counterfeit dental blanks and unqualified counterfeit dental tools can be identified. Thereby, the quality of the dental restorations can be secured, the dental tool machine can be operated more safely, and the user satisfaction can be increased.

According to the present invention, the trained artificial intelligence based identification may be used as the sole means for identifying the dental consumables equipped into the dental tool machine. In this case, the dental tool machine is provided to the end user or customer without any of the auxiliary means—as mentioned before—for recognizing the dental consumables.

According to the present invention, the trained artificial intelligence based identification may be alternatively used to secure the recognition achieved through the auxiliary means in the dental tool machine. A user interface may partly serve as an auxiliary means for recognizing the dental consumables. Alternatively, a reading means may serve as an auxiliary means for recognizing the dental consumables having information tags. Therefore, in alternative embodiments, the dental tool machine is provided with one or more auxiliary means of the above mentioned type. In an embodiment, one or more information tags of the dental consumables are read through a reading means; the type and/or the condition of each dental consumable is recognized based on the read information; and thereafter, it is verified whether the recognition is consistent with the identification. The information tag may be an RFID tag, a QR code, or a bar code. And the reading means may be an RF transceiver, an optical transceiver/receiver, a camera or the like. If the verification is inconsistent, the machining may be inhibited for security. In addition, the machining may be allowed if the consumables are suitable for the forthcoming machining and the verification is consistent. In an alternative embodiment, the information on the dental consumables is input through a user-interface; the dental consumables are recognized based on the inputted information; and, thereafter, it is verified whether the recognition is consistent with the identification. Similar as in the preceding embodiment, the machining may be inhibited for security if the verification is inconsistent. And the machining may be allowed if the consumables are suitable for the forthcoming machining and the verification is consistent.

According to the present invention, the trained artificial intelligence based identification may be preferably checked by the operator for security. Therefore in an embodiment, the user is allowed to check the correctness of the identification, and to correct the identification, if necessary. The check may be carried out via the user-interface. The user-interface preferably has a touch-sensitive display or the like for displaying the identification, and for allowing the user to confirm the correctness of the identification or to input the correct identification through a CAD/CAM software. The machining may be inhibited for security, if the identification is incorrect according to the user. The user may correct the identification before allowing the forthcoming machining. The correction of the identification may also be allowable in case the dental tool machine employs any one of the above-mentioned auxiliary means for the recognition of the dental consumables. In this case, the verification is based on the corrected identification.

According to the present invention, the trained artificial intelligence is preferably implemented through a trained neural network, more preferably through a trained convolutional neural network. The trained neural network is part of the dental machining system. The trained artificial intelligence may be implemented through a computer-implemented algorithm which is preferably part of the CAD/CAM software running on a processing unit or a PC in the dental machining system. In either cases, the trained artificial intelligence may be external or internal to the dental tool machine. In the former case, the trained artificial intelligence may be reached by the dental tool machine over wired and/or wireless communication lines such as the internet or the like. The trained artificial intelligence may be used by more than one dental tool machine. The trained artificial intelligence may be continually trained or updated in view of the dental consumables which become newly available on the market.

According to the present invention, the method has a training phase and an inference phase. In the training phase, the artificial intelligence is trained by the signal indicative of the collision and the recognition through the auxiliary means and/or the user check. The training phase may be performed on a dental machining system including the auxiliary means and/or the user-check feature which are all preferably not provided to the end user. The end user may be provided with the dental machining system including the trained artificial intelligence as the sole means for the identification i.e., without the auxiliary means and/or a user-check feature. Alternatively, the end user may be provided with the dental machining system including any of the auxiliary means and/or the user-check feature in addition to the trained artificial intelligence for the identification. Thereby, the artificial intelligence may be further trained by the user or used for securing the dental tool machine. In the inference phase, the signal indicative of the collision is detected, the detected signal is analyzed through the trained artificial intelligence, the type and/or the condition of at least one of the dental consumables is identified based on the analysis. In the analysis, preferably a Fourier transformation is applied to the signal to generate a frequency spectrogram comprising the spectrum of frequencies versus time. The signal is time dependent. The frequency spectrum serves as a fingerprint. The same analysis is preferably also applied in the training phase.

The present invention also provides a dental machining system which has a dental tool machine. The dental tool machine comprises: consumables including at least one of a dental blank and a dental tool; one or more driving units each movably holding at least one dental tool for machining a corresponding side of the dental blank; a dental blank holder for holding at least one dental blank relatively movably with respect to the dental tools; a detection means for detecting a signal indicative of a collision of the dental tool with the dental blank or the dental blank holder. The dental machining system further comprises means for implementing a trained artificial intelligence that is adapted to analyze the detected signal and identify the type and/or the condition of at least one of the dental consumables based on the analysis; and a control means adapted to control the dental machining system according to the present method. The detection means preferably detects the signal based on the sound of the collision through an acoustic sensor. Alternatively, the speed, the acceleration, the vibration of the respective dental tool, or the force, the torque acting on the respective dental tool, or the supply current to the tool motor of the respective dental tool may be detected by respectively using a speed sensor, an acceleration sensor, a vibration sensor, a force sensor, a torque sensor, or a supply current sensor. Reference values may be used in the detection of the signal.

According to the present invention, the dental machining system preferably has a reading means adapted to read an information tag on the dental consumable, wherein the dental consumable has an RFID tag, a QR code, a bar code or the like. Alternatively, the dental machining system may have a user-interface for inputting the information on the dental consumables.

According to the present invention, the control means may selectively initiate the collision before start of the machining, in a pause in the machining, or after the machining of the dental blank. And the detection means detects the signal accordingly. The collision is preferably initiated when the machine compartment is closed. Thereby, the type and/or the condition of each dental consumable can be initially identified. The condition of the dental tool may be monitored in-between or at the end of machining. The information on the wear condition of the dental tool can be displayed to the user via the user interface and/or stored in the database.

The present invention also provides a computer-program which has computer-readable codes for causing a computer based dental machining system to carry out the method steps of the present invention. This computer-program may also include the algorithm for implementing the trained artificial intelligence. The present invention also provides a computer-readable data storage which stores the computer-program.

BRIEF DESCRIPTION OF THE DRAWINGS

In the subsequent description, further aspects and advantageous effects of the present invention will be described in more detail by using exemplary embodiments and by reference to the drawings, wherein FIG. 1—is a diagram showing the amplitude of the frequency distribution at an arbitrary instant in a signal detected through the method according to an embodiment of the present invention.

DETAILED DESCRIPTION OF THE INVENTION

Figure 3:
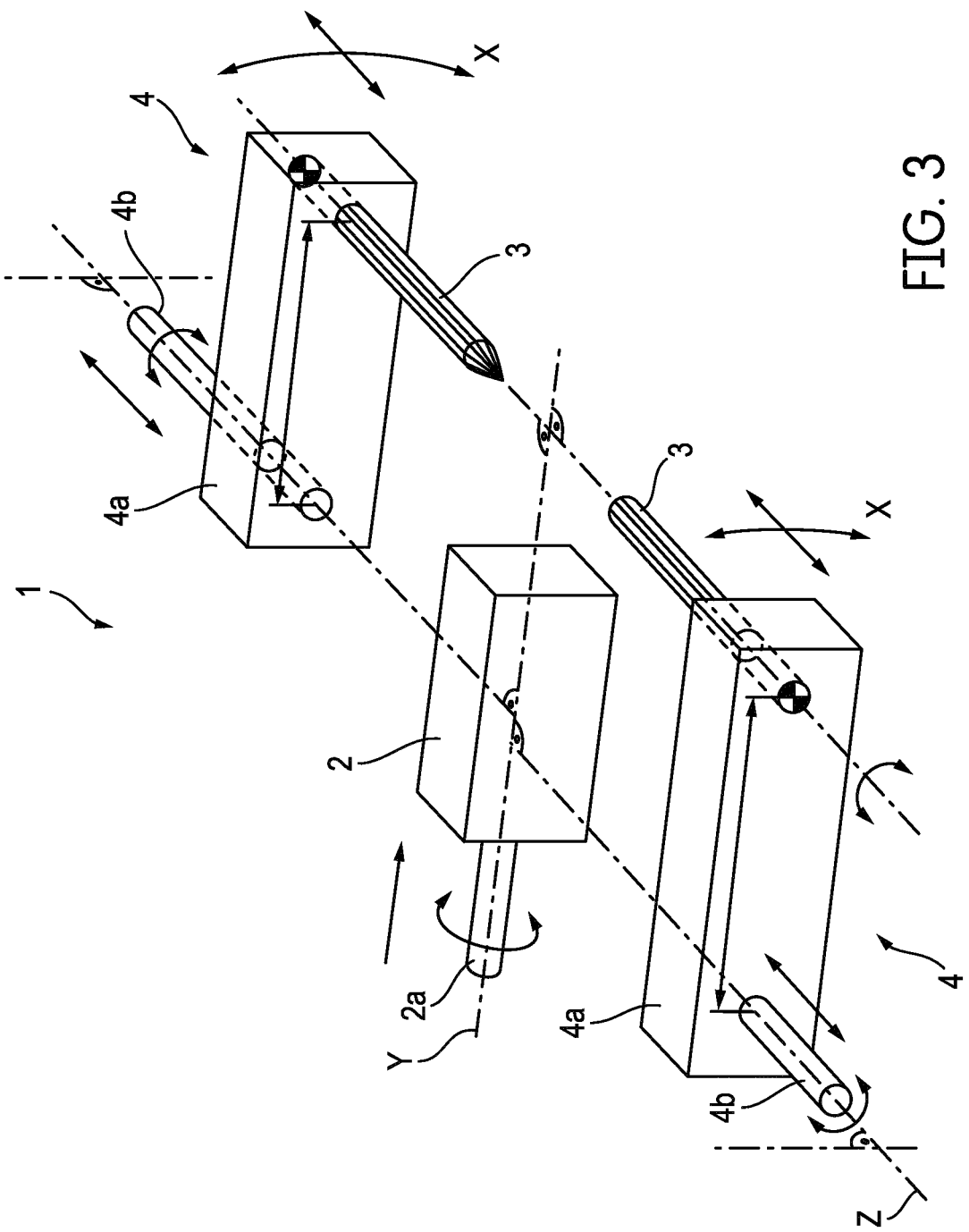
FIG. 3—is a schematic partial view of a dental tool machine of a dental machining system according to an embodiment of the present invention.

The reference numbers shown in the drawings denote the elements as listed below and will be referred to in the subsequent description of the exemplary embodiments:
1. Dental tool machine
2. Dental blank
   2a. Shaft
3. Dental tool
4. Driving unit
   4a. Arm
   4b. Shaft FIG. 3 shows a dental tool machine (1) of a dental machining system according to an embodiment. The dental tool machine (1) comprises: consumables including a dental blank (2) and dental tools (3); two driving units (4) each movably holding a dental tool (3) for machining a corresponding side of the dental blank (2); a dental blank holder for holding the dental blank (2) relatively movably with respect to the dental tools (3); and a detection means for detecting a signal indicative of a collision of the dental tool (3) with the dental blank (2) or the dental blank holder. Each driving unit (4) has a shaft (4b) and an arm (4a) radially fixed to the shaft (4b). Each shaft (4b) can be moved in the z axis through a driving mechanism of the respective driving unit (4). Each arm (4a) can be moved around the z axis through the driving mechanism. The dental tools (3) are mounted to one or more tool motors in each arm (4a) respectively. The dental blank (2) is joined to a shaft (2a) which can be moved in the y axis and rotated around the y axis through another driving mechanism. The dental machining system further comprises means for implementing a trained artificial intelligence that is adapted to analyze the detected signal and identify the type and/or the condition of each dental consumable based on the analysis; and a control means adapted to control the dental machining system according to the method of the present invention. The present method can also be applied to dental tool machines which have a different kinematical structure as that illustrated in FIG. 3.

The method of the present invention serves the purpose of identifying the dental consumables including at least one of a dental blank (2) and a dental tool (3) equipped into the dental tool machine (1). The method comprises: a step of colliding the dental tool (3) with the dental blank (2) or a dental blank holder of the dental tool machine (1); a step of detecting a signal indicative of the collision; a step of analyzing the detected signal through trained artificial intelligence; and a step of identifying the type and/or the condition of at least one of the dental consumables based on the analysis. For the collision, the slowly rotating dental tool (3) is relatively moved against the dental blank (2) or the dental blank holder along the directions x, y, z defined through the axes of freedom as shown in FIG. 3.

Figure 1:
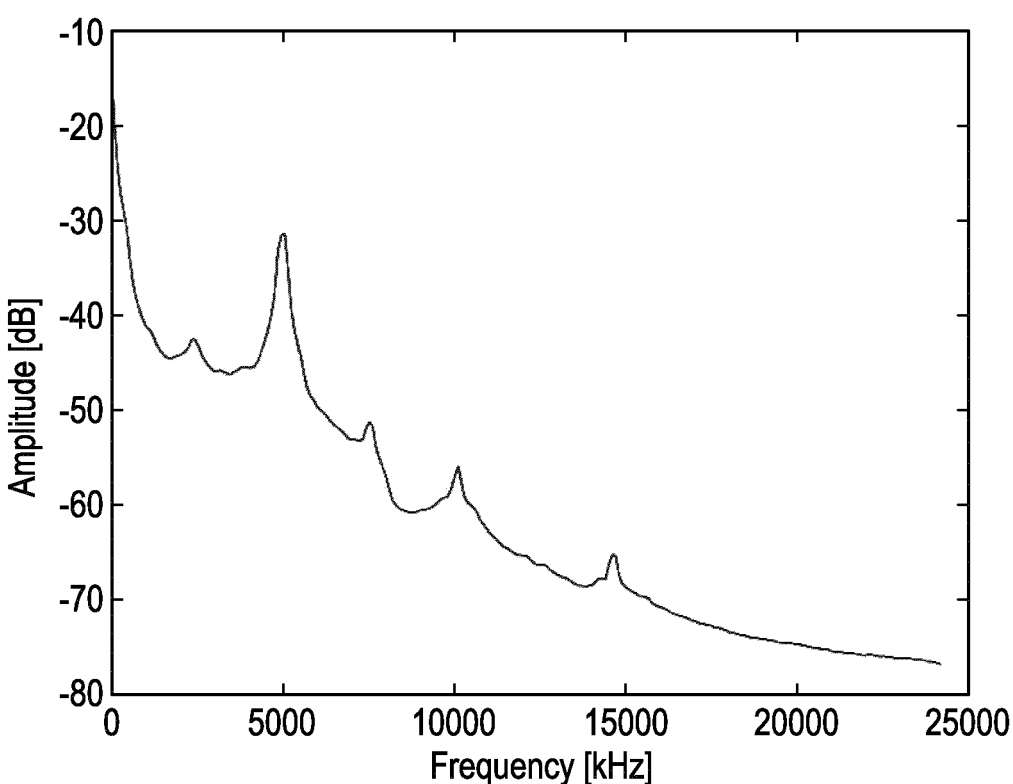
Figure 2:
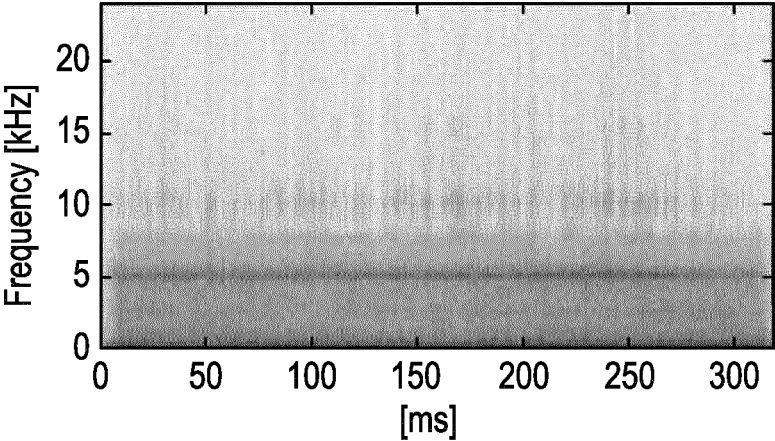
FIG. 2—is a frequency spectrogram showing the spectrum of frequencies with respect to time for a signal detected through the method according to an embodiment of the present invention.

In an embodiment, in the analyzing step a Fourier transformation is applied to the signal to generate a frequency spectrogram comprising the spectrum of frequencies versus time. FIG. 1 shows the amplitudes of the frequency distribution at an arbitrary instant in the signal detected during the collision. FIG. 2 shows a frequency spectrogram i.e., the spectrum of frequencies of the detected signal with respect to time. The frequency spectrogram serves as a fingerprint of the collision to identify the type and the condition of the consumables based on an empirical study for the available consumables on the market. The type of the consumable includes for example the material and the geometrical properties, and preferably the manufacturer. A database is used for the information on the manufacturer and the like. The condition of the consumable includes for example the degree of wear of the dental tool, and the shrinkage of the dental blank. The degree of wear can be shown in percentage. For instance, 100% indicates a new dental tool (3), and 0% indicates a completely worn dental tool (3).

In an embodiment, the collision noise is recorded with a microphone to generate the signal indicative of the collision. The signal is preferably fed to two (analog) filters connected in parallel: 1× high pass filter, 1× low pass filter. A comparator compares the level behind the low pass filter with the level behind the high pass filter. Depending on the output of the comparator, the material of the dental blank (2) may be classified as ceramic or plastic. Thus, in the step of analyzing the signal, high pass filters and low pass filters may be additionally or separately used in the framework of the trained artificial intelligence.

In an embodiment, the trained artificial intelligence is implemented through software, namely through a computer-implemented algorithm. The trained artificial intelligence may be alternatively implemented trough a hardware. The trained artificial intelligence is implemented through a trained neural network, preferably a trained convolutional neural network.

In an embodiment, the control means is further adapted to initiate the collision before start of the machining. Alternatively, or additionally, the control means may initiate the collision in a pause in the machining and/or after the machining of the dental blank. The detection means is further adapted to detect the signal accordingly.

In an embodiment, the detection means is adapted to detect the signal through an acoustic sensor based on the sound of the collision. Alternatively, the detection means may be adapted to detect the signal based on the speed, the acceleration, the vibration of the respective dental tool (3), or the force, the torque acting on the respective dental tool (3), or the supply current to the tool motor of the dental tool (3) respectively through a speed sensor, an acceleration sensor, a vibration sensor, a force sensor, a torque sensor, or a supply current sensor. The speed is preferably the speed of revolution of the dental tool (3). Herein, the speed, acceleration and the force may be measured along any of the x, y, z directions corresponding the degrees of freedom of the dental tool machine (1). Also reference/threshold values may be used in the detection for pre-processing the signal.

In an embodiment, the dental machining system may further comprise a reading means adapted to read an information tag on the dental consumable. In this embodiment, the dental consumable may have an RFID tag, a QR code, a bar code or the like. The information tag may include information on the specification of the dental consumable, such as the type, the manufacturer, the production date, material, geometry, current remaining service life, and the like. The reading means may be an RF transceiver, an optical transceiver, a camera or the like. In this embodiment, the method further comprises: a step of reading one or more information tags of the dental consumables; a step of recognizing the type and/or the condition of each dental consumable based on the read information; and a step of verifying consistency of the recognition with the identification. In this embodiment, the identification may be used to secure the recognition through the verification according to a scenario which will be explained later.

In an embodiment, the dental machining system further comprises a user-interface for inputting information on a dental consumable. The user interface is preferably located on the dental tool machine (1). Alternatively, the user interface may be implemented through a PC connected to the dental tool machine (1). In this embodiment, the method further comprises: a step of inputting into the dental tool machine (1) information on the dental consumables through the user-interface; a step of recognizing the type and/or the condition of each dental consumable based on the inputted information; and a step of verifying consistency of the recognition with the identification. Also, in this embodiment, the identification may be used to secure the recognition through the verification as mentioned above.

In an embodiment, for the purpose of securing the operation of the dental tool machine, in the framework of the above-mentioned scenario, the method further comprises a step of inhibiting the machining for security if the verification is inconsistent. In this embodiment, the method further comprises a step of allowing the machining if the consumables are suitable for the machining and, additionally, the verification is consistent.

In an embodiment, the user can check the identification and correct it, if necessary, via the user-interface. In this embodiment, the method further comprises a step of allowing an operator to check the correctness of the identification, and to correct the identification, if necessary.

In an embodiment, for the purpose of securing the operation of the dental tool machine, in the framework of the above-mentioned scenario, the method further comprises a step of inhibiting the machining for security if the identification is incorrect according to the user-check. In this embodiment, the method further comprises a step of allowing the machining if the consumables are suitable for the machining and, additionally, the identification is correct according to the user-check.

In an embodiment, the method further comprises a step of training the artificial intelligence based on the detected signal and the recognition. In an alternative embodiment, the method further comprises a step of training the artificial intelligence based on the detected signal and the corrected identification. Thereby, the training phase can be supervised and subjected to the correction through the user or operator. In the training phase, the frequency spectrograms serve as fingerprints of the collisions to identify the type and the condition of the consumables. Also, a database for the identity and specification of the available consumables may be used.

The invention claimed is:

1. A method of identifying dental consumables including at least one of a dental blank and a dental tool equipped into a dental tool machine for manufacturing dental restorations, the method comprising:

colliding the dental tool with the dental blank or a dental blank holder of the dental tool machine as part of a touch calibration process executed prior to machining a dental restoration, the touch calibration process to establish a reference value of a dental material type or a dental geometrical property of the dental blank or the dental blank holder;

detecting a signal indicative of the collision;

analyzing the detected signal through trained artificial intelligence;

identifying the material type or geometrical properties of at least one of the dental consumables based on the analysis;

receiving one or more information of the dental consumables respectively;

recognizing the type and/or the condition of each dental consumable based on the received information; and verifying consistency of the recognition with the identification.

2. The method according to claim 1, wherein the information is an information tag that is an RFID tag, a QR code, or a bar code and said information is read in a reading step; and in the reading step an RF transceiver or an optical transceiver/receiver is accordingly used for reading the information tag.

3. The method according to claim 1, further comprising: receiving said information based on inputting into the dental tool machine said information on one or more dental consumables through a user interface.

4. The method according to claim 1, further comprising inhibiting the machining responsive to determining that the verification is inconsistent.

5. The method according to claim 1, further comprising allowing the machining if the consumables are suitable for the machining and the verification is consistent.

6. The method according to claim 1, further comprising determining the correctness of the identification, and correcting the identification responsive to determining that a correction is necessary.

7. The method according to claim 6, further comprising inhibiting the machining responsive to determining that the identification is incorrect.

8. The method according to claim 6 further comprising allowing the machining responsive to determining that the consumables are suitable for the machining and the identification is correct.

9. The method according to claim 6, further comprising training the artificial intelligence based on the detected signal and the corrected identification.

10. The method according to claim 1, further comprising training the artificial intelligence based on the detected signal and the recognition.

11. The method according to claim 1, wherein analyzing comprises applying a Fourier transformation to the signal to generate a frequency spectrogram comprising the spectrum of frequencies versus time.

12. The method according to claim 1, wherein the trained artificial intelligence is implemented through a computer-implemented algorithm based on a neural network.

13. The method according to claim 12, wherein analyzing comprises using a trained convolutional neural network.

14. A non-transitory computer program comprising computer-readable codes for causing a computer based dental machining system for manufacturing dental restorations to perform operations comprising:

colliding a dental tool with a dental blank as part of a touch calibration process executed prior to machining a dental restoration, the touch calibration process to establish a reference value of a dental material type or a dental geometrical property of the dental blank or the dental blank holder;

detecting a signal indicative of the collision;

analyzing the detected signal through trained artificial intelligence;

identifying the material type or geometrical properties of the dental blank based on the analysis;

receiving information of dental consumables;

recognizing the type and/or the condition of each dental consumable based on the received information; and verifying consistency of the recognition with the identification.

15. A non-transitory computer-readable data storage medium storing a program, which, when executed by a computer system for manufacturing dental restorations, causes the computer system to perform operations comprising:

colliding a dental tool with a dental blank or a dental blank holder of a dental tool machine as part of a touch calibration process executed prior to machining a dental restoration, the touch calibration process to establish a reference value of a dental material type or a dental geometrical property of the dental blank or the dental blank holder;

detecting a signal indicative of the collision;

analyzing the detected signal through trained artificial intelligence;

identifying the material type or geometrical properties of the dental blank based on the analysis;

receiving information of dental consumables;

recognizing the type and/or the condition of each dental consumable based on the received information; and verifying consistency of the recognition with the identification.

16. A dental machining system for manufacturing dental restorations comprising:

a dental tool machine which comprises:

dental consumables including at least one of a dental blank and a dental tool;

one or more driving units each movably holding at least one dental tool for machining a corresponding side of the dental blank;

a dental blank holder for holding at least one dental blank relatively movably with respect to the dental tools;

a detection device configured to detect a signal indicative of a collision of the dental tool with the dental blank or the dental blank holder, where the collision is part of a touch calibration process executed prior to machining a dental restoration, the touch calibration process to establish a reference value of a dental material type or a dental geometrical property of the dental blank or the dental blank holder;

means for implementing a trained artificial intelligence that is configured to analyze the signal and identify the material type or geometrical properties of at least one of the dental consumables based on the analysis;

means for receiving information of the dental consumables;

means for recognizing the type and/or the condition of each dental consumable based on the received information;

means for verifying consistency of the recognition with the identification; and a control device configured to control the dental machining system.

17. The dental machining system according to claim 16, wherein the detection device is further configured to detect the signal based on the sound of the collision, or the speed, the acceleration, the vibration of the respective dental tool or the force, the torque acting on the respective dental tool or the supply current to a dental tool motor of the respective dental tool.

18. The dental machining system according to claim 16, further comprising: a reading device configured to read an information tag on the dental consumable, wherein the dental consumable has an RFID tag, a QR code, or a bar code.

19. The dental machining system according to claim 16, further comprising a user interface for inputting information on a dental consumable.

20. The dental machining system according to claim 16, wherein the control device is further configured to initiate the collision before start of the machining, in a pause in the machining, or after the machining of the dental blank, and the detection device is further configured to detect the signal accordingly.

\* \* \* \* \*